(12) United States Patent
Rovani, Jr. et al.

(10) Patent No.: US 7,223,603 B2
(45) Date of Patent: May 29, 2007

(54) CONTINUOUS ON-LINE PROCESS CONTROL OF RESIDUA DISTILLATION

(75) Inventors: Joseph F. Rovani, Jr., Laramie, WY (US); John F. Schabron, Laramie, WY (US); Thomas F. Turner, Laramie, WY (US)

(73) Assignee: University of Wyoming Research Corporation, Laramie, WY (US)

( * ) Notice: Subject to any disclaimer, the term of this patent is extended or adjusted under 35 U.S.C. 154(b) by 0 days.

(21) Appl. No.: 10/374,779

(22) Filed: Feb. 25, 2003

(65) Prior Publication Data
US 2003/0211621 A1 Nov. 13, 2003

Related U.S. Application Data

(60) Provisional application No. 60/379,300, filed on May 10, 2002.

(51) Int. Cl.
*G01N 33/24* (2006.01)
(52) U.S. Cl. .............................. 436/29; 436/50; 436/55; 436/149
(58) Field of Classification Search ................ 436/55, 436/25, 29, 50, 149
See application file for complete search history.

(56) References Cited

U.S. PATENT DOCUMENTS

| | | | |
|---|---|---|---|
| 4,493,765 A | 1/1985 | Long et al. | 208/309 |
| 4,628,204 A | 12/1986 | Maes | 250/343 |
| 4,990,773 A | 2/1991 | Supernaw et al. | |
| 5,092,983 A | 3/1992 | Eppig et al. | 208/323 |
| 5,574,215 A | 11/1996 | Bunger et al. | 73/64.54 |
| 5,861,228 A | 1/1999 | Descales et al. | 436/171 |
| 5,969,237 A | 10/1999 | Jones et al. | |

FOREIGN PATENT DOCUMENTS

WO    WO 00/77120    12/2000

OTHER PUBLICATIONS

Carrier et al. "Acoustic method for measuring asphaltene flocculation in crude oils", Journal of Petroleum Science & Engineerin (2000), 27(3-4), 111-117.*
Chambers et al. Bondline Analysis Using Swept-Frequency Ultrasonic Spectroscopy http://www.southernresearch.org/uspec/Insight0399 PDF, 092/04/1999.*
Schabron et al. "Coking indexes using the Heithaus titration and asphaltene solubility", Preprints—American Chemical Society, Division of Petroleum Chemistry (1999), 44(2), 187-189.*
Jones et al. "Development of an ultrasonic oil stability monitor for the assessment of asphaltene aggregation in hydrocarbon streams", Proceed. Intern. Conf. Mitigat. Heat Exch. Foul. Econ. Envir. Implic. Banff, AB, Canada, Jul. 1999, 84-94.*

(Continued)

Primary Examiner—Yelena G. Gakh
(74) Attorney, Agent, or Firm—Santangelo Law Offices, P.C.

(57) ABSTRACT

Ultrasonic spectroscopy, calorimetry, or thermogravimetric analysis provide measures which correlate with properties of asphaltene complex of petroleum residua which can be used to establish or maintain consistent properties of petroleum residua during blending or to determine immediacy of petroleum residuea to deposition phenomena during pyrolytic thermal treatment.

20 Claims, 7 Drawing Sheets

OTHER PUBLICATIONS

Andersen, S.I. and K.S. Birdi, 1991, "Aggregation of Asphaltenes as Determined by Calorimetry," *Journal of Colloid and Interface Science*, 142, 497-502 1991.

Barton, A.F., 1974, "Solubility Parameters." 1974 *Chemical Reviews*, 75 (6), 731-753.

Burrell, H., 1955, "Solubility Parameters." Spring, 1955, *Interchemical Review*, 3-16.

"Energy and Environmental Profile of the U.S. Petroleum Refining Industry," 1998, Prepared by Energetics Inc. for U.S. Department of Energy Office of Industrial Technologies, pp. 4-5, 27, 33, 49, and 62-63.

Heithaus, J. J., 1962, "Measurement and Significance of Asphaltene Peptization." Journal of the Institute of Petroleum 48 (458), 45-53.

Hildebrand, J.H., J.M. Prausnitz. and R.L. Scott, 1970, "Regular and Related Solutions," Van Nostrand Reinhold, NY, pp. 24-27, pp. 152-153, pp. 212-215.

Long, R.B. and J.G. Speight, 1989, "Studies in Petroleum Composition," *Revue de Institute Francais du Petrole*, 44 (2), 205-217.

Long R.B., 1979, "The Concept of Asphaltenes," *Preprints, Div. Petroleum Chemistry, American Chemical Society*, 24, 891-901.

Magaril, R.Z., E.I. Aksenova, 1968, "Study of the mechanism of Coke Formation in the Cracking of Petroleum Resins," International Chemical Engineering (vol. 8, No. 4), 1 page.

Pauli, A.T., 1996 "Asphalt Compatibility Testing Using the Automated Heithaus Titration Test," *Preprints, Division of Fuel Chemistry, American Chemical Society*, 41 (4), 1276-1281.

Scatchard, G., 1931, "Equilibria in Non-Electrolyte Solutions in Relation to the Vapor Pressure and Densities of the Components," *Chemical Reviews*, 321-333.

Schabron, J.F., A. Troy Pauli, Joseph F. Rovani, Jr., Francis P. Mikins, 2000 "Deposition from Heavy Oils," Department of Energy Report DE-FC26-98FT40322, 35 pages.

Schabron, J.F., A Troy Pauli, Joseph F. Rovani, Jr., 2001 "Molecular Weight Polarity Map for Residua Pyrolysis" Fuel 80 529-537.

Schabron, J.F., A. Troy Pauli, Joseph F. Rovani, Jr., 2001 "Nonpyrolytic Heat Induced Deposition from Heavy Oils," Fuel 80 919-928.

Schabron, J.F., A. Troy Pauli, Joseph F. Rovani, Jr., Francis P. Mikins, 2001, "Predicting Coke Formation Tendencies," Fuel 80 1435-1446.

Schabron, J.F., A. Troy Pauli, Joseph F. Rovani, Jr., 1999 "Petroleum Residua Solubility Parameter/Polarity Map: Stability Studies of Residua Pyrolysis," Department of Energy Report DE-FC26-98FT40322 Task, 1.2, 24.

Schabron, J.F., and J. G. Speight, 1998, "The Solubillity and Three-Dimensional Structure of Asphaltenes," *Petroleum Science and Technology*, 16 (3-4), 361-376.

Schabron, J.F., G. W. Gardner, J.K. Hart, N.D. Niss, Miyake, and D.A. Netzel, 1993, "The Characterization of Petroleum Residua," US Department of Energy Report DE-MC/11076-3539, 9 pages.

Schabron, J.F., J.R. Rovani, Jr., T.F. Turner, 2002, "Thermal Analysis for Monitoring Incipient Coke Formation", US Department of Energy Report DE/FG36/01G011018, 18 pages.

Small, P.A., 1953, "Some Factors Affecting the Solubility of Polymers" *Journal of Applied Chemistry*, 71-80.

Snyder, L.R., 1968, "Principles of Adsorption Chromatography", Marcel Dekker, Inc., New York, 206-210.

Wiehe, I.A., 1996, "Two-Dimensional Solubility Parameter Mapping of Heavy Oils," *Fuel Science and Technology International*, 14 (1&2), 289-312.

"Standard Test Method for Molecular Weight (Relative Molecular Mass) of Hydrocarbons by Thermoelectric Measurement of Vapor Pressure," ASTM Designation: D 2503—82 (Reapproved 1987), 211-213.

David Julian McClements, "Ultrasonic Measurements in Particle Size Analysis", University of Massachusetts, Amherst, USA, *Encyclopedia of Analytical Chemistry (Applications, Theory and Instrumentation)* pp. 5581-5587.

Waterman, P.C. Truell, Rohn, "Multiple Scattering of Waves", Journal of Mathematical Physics, Jul.-Aug., 1961, pp. 512-537.

Cartz, Louis, ch. 3, "Ultrasonic Testing", Nondestructive Testing, 1995, pp. 81-98.

Schabron, John F., et al., "Characterization of Residua During Pyrolysis", American Chemical Society, vol. 47, No. 1, Feb. 2002, pp. 17-21.

Ulrich Riebel, Loffler, Friedrich, "The Fundamentals of Particle Size Analysis by Means of Ultrasonic Spectrometry", Part. Part. Syst. Charact. 6, 1989, pp. 135-143.

Povey, Malcolm J. W., "Ultrasonic Techniques for Fluids Characterization" 1997.

Kaatze, U., et al., "Acoustical Absorption Spectroscopy of Liquids Between 0.15 and 3000 MHz: I. High Resolution Ultrasonic Resonator Method", J. Phys. E: Sci. Instrum. 1988, pp. 1025-1030.

Kaatze, U, et al., "Acoustical Absorption Spectroscopy of Liquids Between 0.15 and 3000 MHz: II. Ultrasonic Pulse Transmission Methods", J. Phys. E: Sci. Instrum. 1986, pp. 98-103.

Kaatze, U., et al., "Acoustical Absorption Spectroscopy of Liquids Between 0.15 and 3000 MHz: III. Hypersonic Comparator Technique", J. Phys. E: Sci. Instrum. 1987, pp. 402-406.

Kaatze, U., et al. "Broadbond Study of the Scattering of Ultrasound by Polystyrene-latex-in-water Suspsnsions" Annalen der Physik, 1996, pp. 13-33.

Schabron, John F., "The Solubility and Three-Dimensional Structure of Asphaltenes", Petroleum Science and Technology, 16(3&4), 1998, pp. 361-375.

McClements, David Julian, "Ultrasonic Characterization of Emulsions and Suspensions", Advances in Colloid and Interface Science, 37, 1991, pp. 33-72.

Challis, Richard E., et al., "A Wide Bandwidth Spectrometer for Rapid Ultrasonic Absorption Measurements in Liquids", Journal of the Acoustical Society of America, vol. 90, No. 2, Pt. 1, Aug. 1991, pp. 730-740.

Epstein, Paul S., et al., "The Absorption of Sound in Suspensions and Emulsions. I. Water Fog in Air", Journal of the Acoustical Society of America, vol. 25, No. 3, May 1953, pp. 553-565.

Allegra, J. R., et al., "Attenuation of Sound in Suspensions and Emulsions: Theory and Experiments", Journal of the Acoustical Society of America, vol. 51, No. 5, pt. 2, pp. 1545-1564.

Hemar, Y., et al., Effective Medium Model for Ultrasonic Attenuation Due to the Thermo-Elastic Effect in Concentrated Emulsions, Journal De Physique II, Apr. 1997, pp. 637-647.

McClements, D. J., et al., "Scattering of Ultrasound by Emulsions", J. Phys. D: Appl. Phys. vol. 22, 1989, pp. 38-47.

Schabron, John F., et al., "Predicting Proximity to Coke Formation", PCT US00/15950, filed Jun. 9, 2000, 59 pages, 13 pages of drawings.

U.S. National Stage Application, entitled "Predicting Proximity to Coke Formation", U.S. Appl. No. 10/009,863, filed Dec. 10, 2001, 59 pages and 13 sheets of drawings.

U.S. Provisional Application, entitled "Continuous On-Line Process Control of Residua Distillation", U.S. Appl. No. 60/379,300, filed May 10, 2002, 16 pages and 6 sheets of drawings.

U.S. Provisional Application, entitled, "Automated Flocculation Titrimeter System", U.S. Appl. No. 60/266,555 filed Feb. 5, 2001.

U.S. PCT Application entitled "Automated Flocculation Titrimeter System", PCT/US02/03983, filed Feb. 5, 2002.

U.S. Provisional Application entitled "Predicting Proximity to Coke Formation", U.S. Appl. No. 60/138,846, filed Jun. 10, 1999.

\* cited by examiner

FIG 1

Weight Percent Coke vs. $p_a/C_{min}$

FIG 2

Weight Percent Coke vs. Y/X

FIG 3

Heat Capacities from Differential Scanning Calorimetry

FIG 4

WRI Coking Indexes vs. Heat Capacity

FIG 5

Thermogravimetric Analysis Profiles

FIG 6

Differential Plot of Thermogravimetric Analysis

FIG 7

CONTINUOUS ON-LINE PROCESS CONTROL OF RESIDUA DISTILLATION

This application claims the benefit of U.S. patent application Ser. No. 60/379,300, filed May 10, 2002, hereby incorporated by reference herein.

FIELD OF THE INVENTION

Ultrasonic spectroscopy, differential scanning calorimetry, or themogravimeteric analysis of petroleum residua during thermal treatment provide measures that allow on-line determination of immediacy of such petroleum residua to coke formation.

BACKGROUND OF THE INVENTION

Petroleum residua consist of an ordered continuum of solvated polar materials usually referred to as asphaltenes dispersed in a lower polarity solvent phase held together by intermediate polarity materials usually referred to as resins.

Refinery processing of petroleum residua such as heavy oils, shale oils, coal tars, tar sand bitumen, asphalts, or the like, to obtain lighter distillate fuels require heating for distillation, hydrogen addition, or carbon rejection (coking). Typically, refinery processing does not include the addition of solvents, non-solvents, precipitation agents, flocculation agents, or the like to petroleum residua during heating. Efficiency of such refinery processing can be limited by the formation of insoluble carbon-rich materials such as coke as the amount of resins are depleted. Heat exchangers and other refinery units must be shut down for mechanical coke removal, resulting in a significant loss of output and revenue. When a petroleum residuum is heated above the temperature at which pyrolysis occurs (greater than about 340° C., 650° F.), there is typically an induction period before coke formation begins. To avoid fouling of refinery equipment, refiners often stop heating a petroleum residuum based upon arbitrary criteria before coke formation begins. Because arbitrary criteria are used thermal treatment is stopped sooner than is necessary, resulting in less than maximum product yield.

The coking indexes disclosed in U.S. patent application Ser. Nos. 60/138,846; 10/009,863, now U.S. Pat. No. 6,373,921, and International Patent Application No. PCT US00/15950, each hereby incorporated by reference herein, can be used by refiners to assess immediacy of petroleum residua to the threshold of coke production. U.S. Pat. No. 6,773,921 discusses various ways to analyze coke formation such as but not limited to coking indexes, filtration, asphaltene flocculation titration, solubility characteristics of asphaltenes, values of a weight percent of a cyclohexane soluble portion of heptane asphaltenes, relative viscosity, $K_S$ values, $K_F$ values, and K values. As such, refiners can thermally treat petroleum residua to the threshold, but not beyond the point at which coke formation begins to form when petroleum residua materials are heated at pyrolysis temperatures. See also, Schabron, J. F., A. T. Pauli, and J. F. Rovani, Jr., "Molecular Weight/Polarity Map for Residua Pyrolysis", *fuel*, 80 (4), 529–537 (2001); Schabron, J. F., A. T. Pauli, and J. F. Rovani, Jr., "Non-Pyrolytic Heat Induced Deposition from Heavy Oils", *Fuel*, 80 (7), 919–928 (2001); and Schabron, J. F., A. T. Pauli, J. F. Rovani, Jr., and F. P. Miknis, "Predicting Coke Formation Tendencies", *Fuel*, 80 (11), 1435–1446 (2001), each hereby incorporated by reference herein.

The development of such coking indexes provide universal predictors provide a solution to the long standing, but unresolved problem of determining immediacy of a petroleum residua to coke formation during petroleum residua refining. As such, these coking indexes have great potential value in improving the efficiency of thermal treatment of petroleum residua during distillation or other processes.

Prior to the instant invention, there were unresolved limitations with respect to the use of these coking indexes. First, the determination of the various coking indexes was by either titration or by solubility measurements performed in a laboratory. See for example, U.S. patent application Ser. No. 60/266,555 and International Patent Application No. PCT US02/03983, each hereby incorporated by reference herein. Secondly, because these coking index determinations are made off line an amount of time elapse prior to obtaining the results which may not then accurately reflect the then existing properties of the petroleum residuum which has continued along in the thermally treatment process. As such, to avoid formation of coke, or other solid material, from petroleum residue undergoing pyrolytic thermal treatment, thermal treatment may have been stopped, or the manner of thermal treatment may have been altered to compensate for the delay in obtaining coking indexing determinations.

When distillation is stopped sooner than is necessary to avoid coke formation, it can result in less than maximal product yield from the hydrocarbon material. In 1997, for example, the average United States atmospheric and vacuum distillation refinery capacity was about 23 million barrels per day as disclosed by the Department of Energy, *OIT Report*, p. 5, (1998), hereby incorporated by reference. Solvent deasphalting capacity was about 0.3 million barrels per day. About 1.8 million barrels per day of heavy end feedstocks produced in 1997 from atmospheric and vacuum distillation columns and solvent-deasphalting units were input to thermal cracking and coking operations. This represents about 10% of the crude run. Id. at p. 49. An additional 6.5 million barrels per day went into catalytic cracking and hydro treating units. Based on the total of 1.8 million barrels of total heavy ends minus about 0.3 million from solvent deasphalting, about 1.5 million barrels of heavy ends per day of thermal cracking and coking feed are produced from distillation operations. Assuming a one percent increase in United States distillate output because of efficiency improvements, an increase of about 15,000 average barrels per day of distillate and a corresponding reduction of heavy ends would result. Efficiency increases well above 1% could be possible if the immediacy to coking for a petroleum residua could be determined on-line to avoid interruption of thermal treatment prematurely.

Moreover, coking operations use about 166,000–258,000 Btu per barrel of petroleum residua feed. Department of Energy, *OIT Report*, pp. 62–63, (1998). Hydrotreater energy use is comparable, and a similar consideration may apply. Since most of the energy used is to initially heat all of the petroleum residua feed material for distillation, there may be only minimal extra heat required to obtain a 1% improvement of distillate output at a particular temperature. For each 1% decrease in hydrocarbon material feed, there would be a potential savings of about 2.5–3.9 billion Btu with respect to petroleum residua feed that do not need to be heated, since they will have been recovered in an optimized distillate stream.

Another significant problem with conventional technology for the evaluation and processing of petroleum residua may be high emissions. An energy savings of about 2.5–3.9 billion Btu per day, as discussed above, can result in a corresponding lowering of emissions from fuel that is not burned in processing operations. For example, residual fuel used as the heat source produces about 174 pounds of carbon dioxide per million Btu generated Department of Energy, *OIT Report*, pp. 27, (1998). Thus, in the U.S., the reduction in carbon dioxide emissions for each 1% industry-wide efficiency improvement may be about 218–679 tons per day!

Another significant problem with conventional technology for the evaluation and processing of petroleum residua may be financial losses. The disruption of petroleum residua processing from fouling due to deposition of solid material, such as coke, is pervasive throughout the industry. The financial losses due to unscheduled downtime events as a result of non-pyrolytic, or of pyrolytic, deposition of carbon rich materials such as coke, may be difficult to quantify, but they are important.

Another significant problem with conventional technology for the evaluation and processing of petroleum residua may be that the liquid products of distillation may be of lower quality. Interrupting the distillation process, or proceeding with the distillation process in steps or stages, to avoid deposition of carbon rich materials or coke may allow for contamination of the liquid distillates.

The invention addresses the various problems associated with determination of coking indexes in the laboratory by providing apparatus and methods that can provide continuous on-line monitoring of petroleum residua processing to avoid coke formation.

SUMMARY OF THE INVENTION

Accordingly a broad object of the invention can be to provide apparatus or methods of refinery process control for petroleum residua to avoid, time, delay or otherwise control the formation of solid material(s) during thermal treatment of petroleum residua.

Another significant object of the invention can be to provide apparatus or methods which provide on-line determination of coking indexes which can reduce or eliminate the need for performing titration or solubility measurements.

Another significant object of particular embodiments of the invention can be to provide ultrasonic spectroscopy apparatus and methods of ultrasonic spectroscopy which provide information corresponding to the relative depletion of intermediate polarity materials or resins in petroleum residua during thermal treatment.

Another significant object of particular embodiment of the invention can be to provide calorimetry apparatus and methods of calorimetry which provide information corresponding to the relative depletion of intermediate polarity materials or resins in petroleum residua during thermal treatment.

Another significant object of particular embodiment of the invention can be to provide thermogravimetric apparatus and methods of calorimetry which provide information corresponding to the relative depletion of intermediate polarity materials or resins in petroleum residua during thermal treatment.

Naturally, further objects of the invention are disclosed by the drawings and the descriptions set forth below.

DETAILED DESCRIPTION OF THE DRAWINGS

DETAILED DESCRIPTION OF PREFERRED EMBODIMENT

Generally, the invention provides methods and apparatus for continuous on-line analysis of petroleum residua during pyrolytic thermal treatment which can provide refinery process control to avoid coke formation.

As discussed above a petroleum residuum that can be analyzed in accordance with the invention includes a wide variety of petroleum residuum commonly referred to as resids or blends thereof; heavy oils; fuel oil that remains after the removal of lighter distillates; or oils obtained from shale or tar sand bitumen; coal tars; asphalts; or other similar pyrolytic materials which form or deposit solid materials upon thermal treatment. As such, the terms "petroleum residuum" or "petroleum residua" along with the various examples of specific petroleum residua provided in this description are not meant to limit the breadth of the invention but are meant to be illustrative of the numerous and wide variety of pyrolytic materials with which the invention is compatible.

The terms "production", "deposition", "deposition phenomena" or "formation" of "solid material(s)" due to pyrolysis of a petroleum residua means the product generated due to pyrolysis of a petroleum residuum and can specifically mean the formation of suspended particulates, the actual precipitation of carbon rich material, coke formation, coke deposition, or the like. These terms are not meant to limit the invention in a manner that requires the solid material(s) generated by a pyrolytic process to be disposed in any particular fashion but rather are meant to be indicative of the transition of the petroleum residuum from a heterogeneous material to homogeneous material.

The term "solid material" in accordance with the invention can mean any amount of, or kind of, material generated by pyrolysis of a petroleum residuum such as coke, or other carbon rich material.

Pyrolysis of small amounts of petroleum residua for experiments can be performed with 80 g sample portions of a petroleum residuum weighed into 12" long×1.4" o.d. stainless steel reactor tubes with a 120 cc volume capacity. The tube is capped and atmospheric air evacuated using a vacuum pump. The reactor tube is then pressurized to 100 psig with nitrogen and leak checked in water. The reactor tube is evacuated again and pressurized with 10 psig of nitrogen for the pyrolysis experiment in a 400° C. (750° F.) fluidized sand bath. Two reactor tubes containing residua and a third containing a thermocouple were run simultaneously in a tube rack. Timing was started when the thermocouple temperature equaled the set point temperature. The rack was removed and cooled by immersing it in another fluidized sand bath at room temperature. The reaction products are poured into glass vials and stored under nitrogen in a refrigerator prior to analysis.

Gravimetric measurements can be obtained by taking aliquots of the stirred reaction products which are then dissolved in toluene and filtered using 10 micron PTFE filters to obtain a gravimetric measurement of toluene insolubles (coke).

Figure 1:
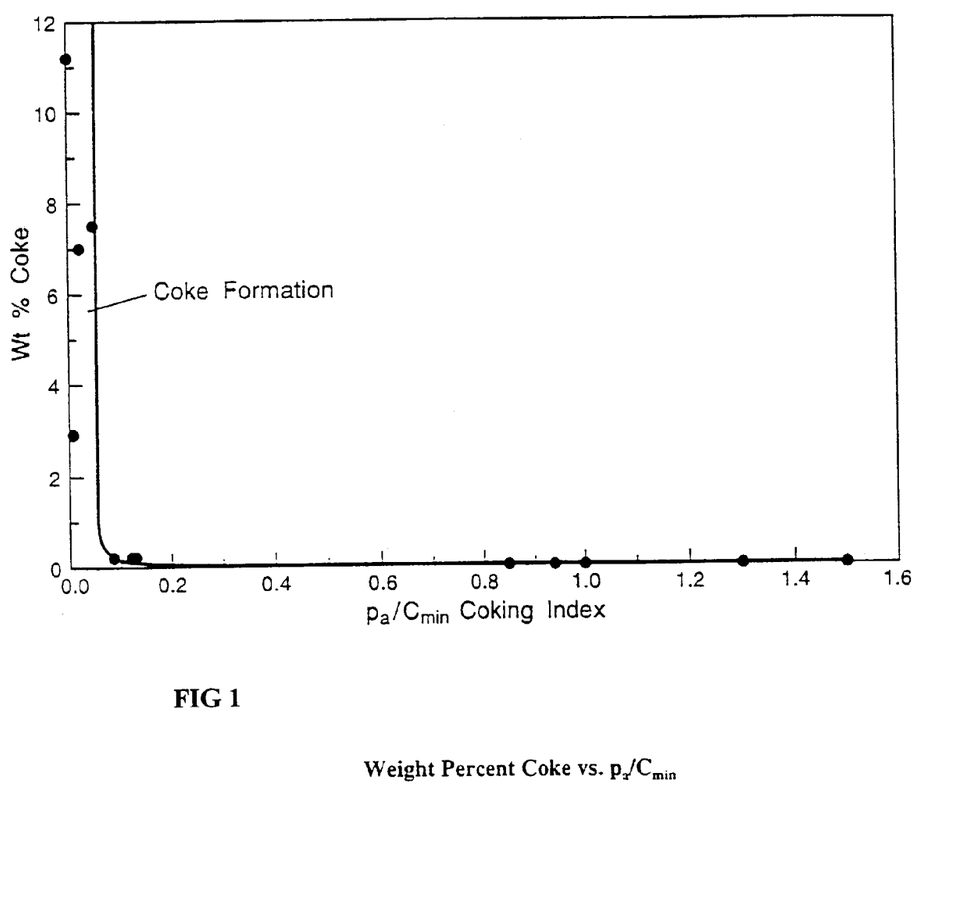
FIG. 1 provides a graph of weight percent coke versus $P_d/C_{min}$.

Now referring primarily to FIG. 1, a coking index can be defined as the ratio of the Heithaus parameters, $p_a/C_{min}$ from an asphaltene flocculation titration as disclosed by Schabron, J. F., A. T. Pauli, J. F. Rovani, Jr., and F. P. Miknis, 2001c, Predicting Coke Formation Tendencies, *Fuel*, 80 (11), 1435–1446, hereby incorporated by reference herein. As pyrolysis progresses, $P_a$ decreases as the polarity of the asphaltenes increases, and $C_{min}$ increases as the overall stability of the petroleum residuum matrix decreases.

Figure 2:
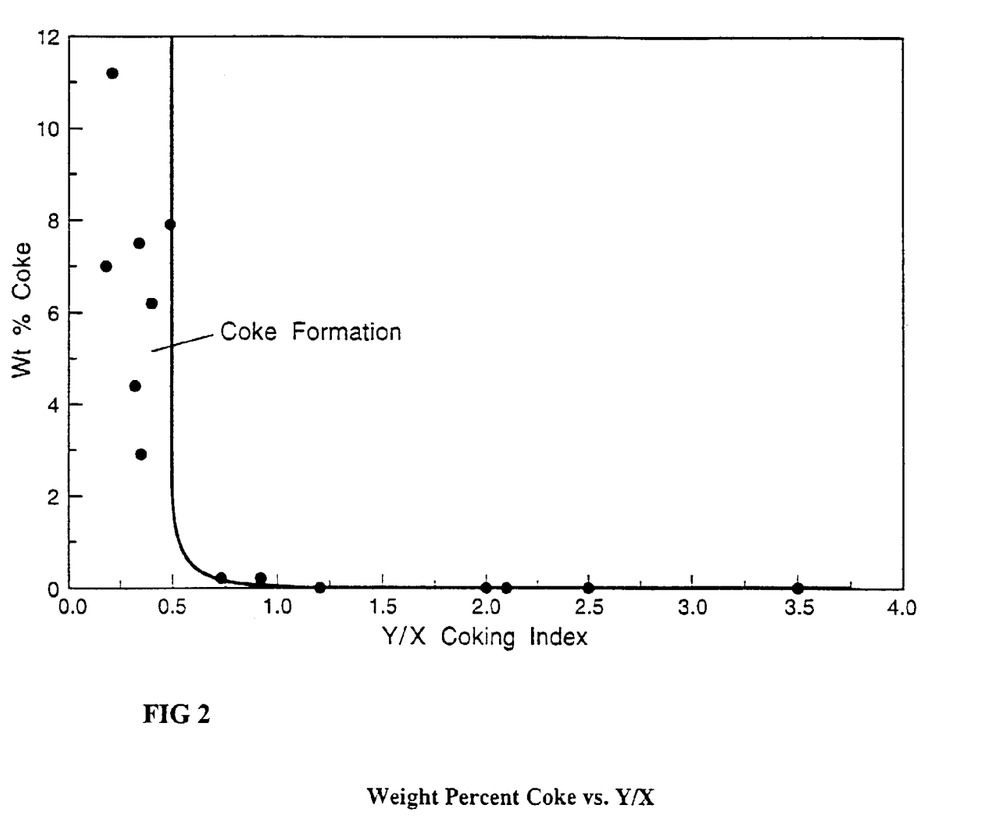
FIG. 2 provides a graph of weight percent coke versus Y/X, where (Y) is the weight percent of the cyclohexane soluble portion of heptane asphaltenes and (X) is the weight percent of heptane asphaltenes.

Now referring primarily to FIG. 2, a second coking index can be established by the ratio of the weight percent of the cyclohexane soluble portion of heptane asphaltenes (Y) to the weight percent of heptane asphaltenes (X). The amount of cyclohexane soluble components of the asphaltenes is diagnostic of the state of the solubilizing resins in these materials. The disappearance of the cyclohexane soluble portion of heptane asphaltenes is coincidental with the onset of coke formation. The Y/X ratio yields a coking index value comparable in magnitude to the $p_a/C_{min}$ ratio. Ratios above 1 indicate relatively stable systems. As pyrolysis progresses, the ratios decrease.

Heptane asphaltenes can be isolated by heating a 40:1 (v:w) mixture of reagent-grade heptane and a petroleum residuum to 70° C. (158° F.) for about ½ hour while stirring, followed by overnight stirring at room temperature. The stirring stopped for 30 minutes prior to filtering. Vacuum filtration can be performed using Ace, 140 mL, 10–20 micron, sintered glass filters. Residual solvent was removed from the asphaltenes on filters using a vacuum oven set at 120° C. (248° F.) for 30 minutes. The asphaltenes were cooled in a desiccator and weighed.

To determine the cyclohexane soluble portion of heptane asphaltenes, a portion of heptane asphaltenes can be ground to a fine powder using a mortar and pestle. A 0.5 g portion of ground heptane asphaltenes is then stirred overnight with 100 mL of cyclohexane. The stirring stopped 30 minutes prior to vacuum filtering using Ace, 140 mL, 10–20 micron, sintered glass filters. Solvent can be removed from the filtrate by rotary evaporation, and traces of cyclohexane are removed using a vacuum oven at 100° C. (212° F.) for 15 minutes. The cyclohexane solubles were cooled in a desiccator and weighed.

As can be understood by FIGS. 1 and 2 as the coking indexes approach their threshold values, coke formation begins. The coking indexes do not predict how much coke will be formed, but only when coking is likely to begin as described by U.S. patent application Ser. Nos. 60/138,846 and 10/009,863, now U.S. Pat. No. 6,773,921; and International Patent Application No. PCT US00/15950, each hereby incorporated by reference herein, and by the further descriptions provided below. The two coking indexes can used as comparative measures to validate the calorimetry, themogravimeteric, or ultrasonic measures described below.

An example of the utility of the two coking indexes, portions of a Lloydminster vacuum residuum were pyrolyzed at 400° C. (750° F.) for residence times of 15, 30, 60, and 80 minutes. The pyrolysis results and the corresponding Coking Indexes data are provided in Table 1.

TABLE 1

Western Research Institute "(WRI") Coking Indexes and Amount of Coke Formed after Pyrolysis at 400° C.

| Pyrolysis Time, | | WRI Coking Indexes | |
|---|---|---|---|
| Minutes | Wt. % Coke | $p_a/C_{min}$ | Y/X |
| 0 | <0.03 | 1.6 | 2.9 |
| 15 | <0.03 | 0.67 | 1.6 |
| 30 | <0.03 | 0.33 | 1.0 |
| 60 | 4.2[b] | 0.04 | 0.6 |
| 80 | 5.9[a], 8.0[b] | — | 0.5 |

[a]Coke amount one day after pyrolysis
[b]Coke amount two weeks after pyrolysis

The vacuum residuum prior to thermal treatment and the vacuum residuum after 15 and 30 minute of thermal treatment contained <0.03 wt. % coke. The 60 and 80 minute products contained 4.2 and 8.0 wt. % coke, respectively.

Figure 3:
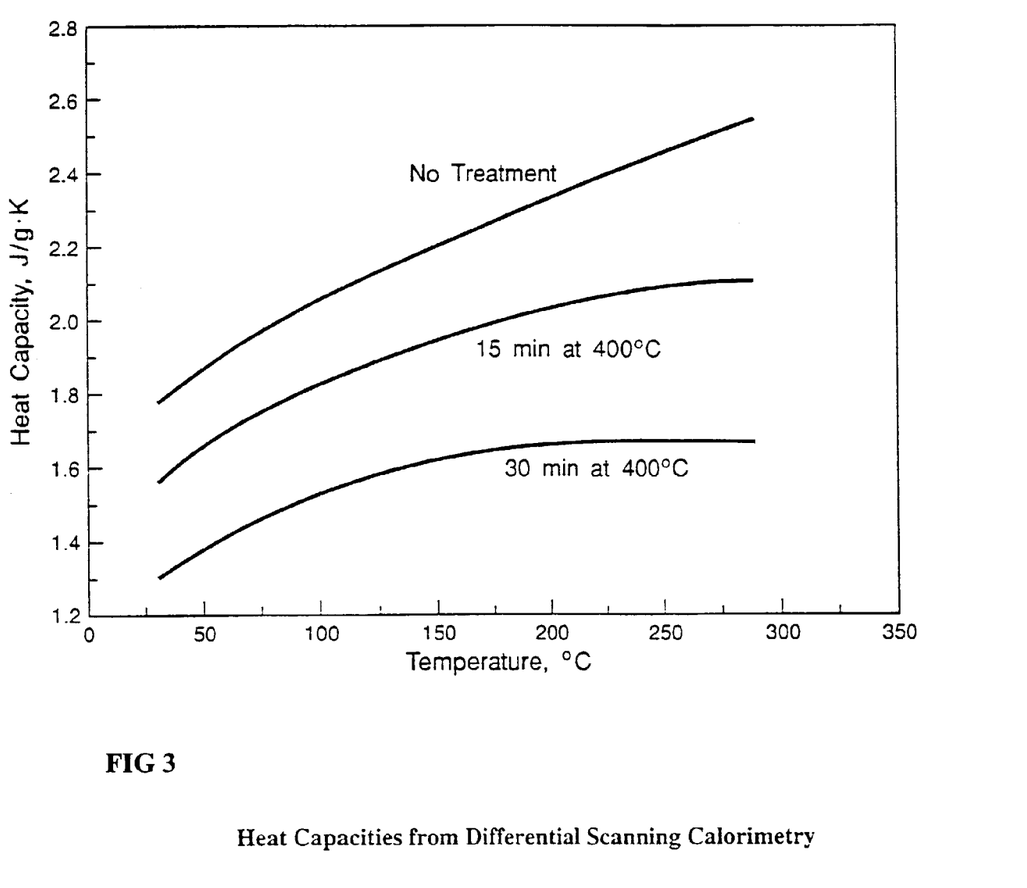
FIG. 3 provides a graph of heat capacities from differential scanning calorimetry.
Figure 4:
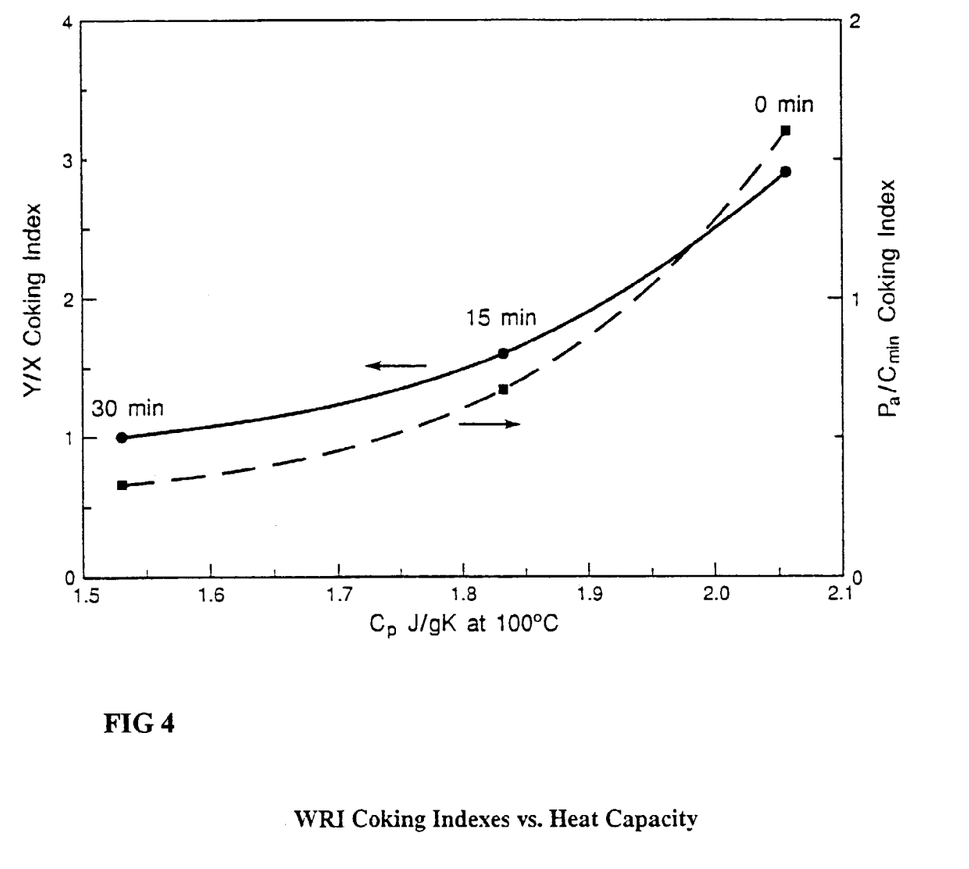
FIG. 4 provides a graph of coking indexes versus heat capacity.

Now referring primarily to FIGS. 3 and 4, an embodiment in accordance with the invention can comprise an amount of petroleum residua responsive to a regulated heat source. The petroleum residua is thermally treated to generate lighter distillates by adjusting the temperature of the petroleum residua typically within the range of ambient temperature to about 650° F. (about 340° C.). In certain cases, however, the temperature may be greater than 650° F. (about 340° C.).

As can be understood from FIG. 3, the heat capacity characteristics of the petroleum residuum during thermal treatment are altered as lighter distillates are removed. The alteration of heat capacity characteristics can be measured using calorimetry. While an number of calorimeters or heat capacity analyzers may be suitable to measure the change in $C_p$ J/gK at a given temperature, differential scanning calorimeters (which may be modulated or unmodulated) having a cell which measures the differential heat flow between a sample and a reference are suitable.

Differential Scanning Calorimetry (DSC) measurements can be performed over the temperature range of 30° C. to 290° C. using a TA Instruments 2920 modulated differential scanning calorimeter (DSC). TA Instruments, 109 Lukens Drive, New Castle, Del. 19720. Average heating rates were 2° C. per minute. The modulation amplitude can be ±0.5° C., and the modulation period can be 80 seconds. Hermetic pans can be used for both sample and reference, a pinhole in each of the lids allows pressure equalization with the DSC cell. The TA2920 DSC is calibrated using standard procedures. Three materials can be used for temperature calibration: indium (mp156.60° C.), water (mp 0.01° C.), and n-octane (mp-56.76). Enthalpy can be calibrated using an indium metal standard (heat of fusion 28.57 J/g). Heat capacity can be calibrated using sapphire. Helium can be used to purge the DSC cell.

Again referring to FIG. 3, the heat capacity profiles for one untreated and two thermally treated samples pyrolyzed for 15 and 30 minutes of Lloydminster vacuum residuum were examined by differential scanning calorimetry. None of the three samples were producing coke. Samples pyrolyzed for longer periods that produced coke were not evaluated since these multi-phase systems are difficult to obtain a representative sample in the 1–5 mg range from.

There are distinct differences among the profiles that are dependent on pyrolysis. Higher severity pretreatment generates products with lower heat capacity. All three samples lost weight through vaporization of light hydrocarbons at the higher temperatures. Some of the curvature of the heat capacity profiles above 100° C. is due to this loss. At 290° C. the losses were 3.2, 16.6, and 18.4 wt. % for the original, 15 minutes, and 30 minutes pyrolysis oils, respectively.

Now referring primarily to FIG. 4, the heat capacities of the three samples of Lloydminster vacuum residuum taken at 0 minutes, and after 15 minutes and 30 minutes of pyrolytic treatment were examined by differential scanning calorimetry at 100° C. and the results are shown by Table 2.

TABLE 2

Heat Capacities for Original and Pyrolyzed Residua

| Pyrolysis Time, min | $C_p$ at 100° C., J/g K |
|---|---|
| 0 | 2.06 |
| 15 | 1.83 |
| 30 | 1.53 |

The determined heat capacities of the three samples are plotted against the determined coking indexes pa/Cmin and Y/X of the samples showing that the change in heat capacity of petroleum residua during pyrolytic thermal treatment can be correlated with the change in the two coke indexes during pyrolytic treatment.

Heat capacity determinations made during petroleum residua processing can provide assessment of immediacy of a petroleum residua to formation of coke when compared directly to either standard heat capacity curves for a particular residuum or correlated with either or both of the two coke indexes.

As such, on-line monitoring which can be continuous during pyrolytic thermal treatment of a petroleum residua can be achieved by further including a petroleum residua sampler which interacts with the petroleum residua to provide aliquots of petroleum residua to the calorimetry cell. In certain embodiments, the petroleum residua sampler can comprise manual sampling to obtain aliquots of the petroleum residua being thermally treated. In other embodiments of the invention this can include a flow regulated conduit between the thermally treated petroleum residua heat capacity analyzer or the cell of a calorimeter. Understandably, the calorimeter could be integral to the thermal processing equipment and information for assessment could be transmitted to location a distance away from the thermal processing equipment. Alternately, assessment as to immediacy of a petroleum residua can be used in an automated feed back loop to provide for continuous thermal treatment of petroleum residua to the threshold of, but not beyond the threshold of, coke formation.

A second manner of analyzing immediacy of a petroleum residua to solids or coke formation during pyrolytic thermal treatment can be by thermogravametric analysis (TGA). Thermogravimetric analysis profiles were obtained with a TA Instruments model TGA 2950 Thermogravimetric Analyzer. Sample weight was 15–30 mg. Samples were heated under a nitrogen sweep from 20° C. to 600° C. at a rate of 10° C./min.

Figure 5:
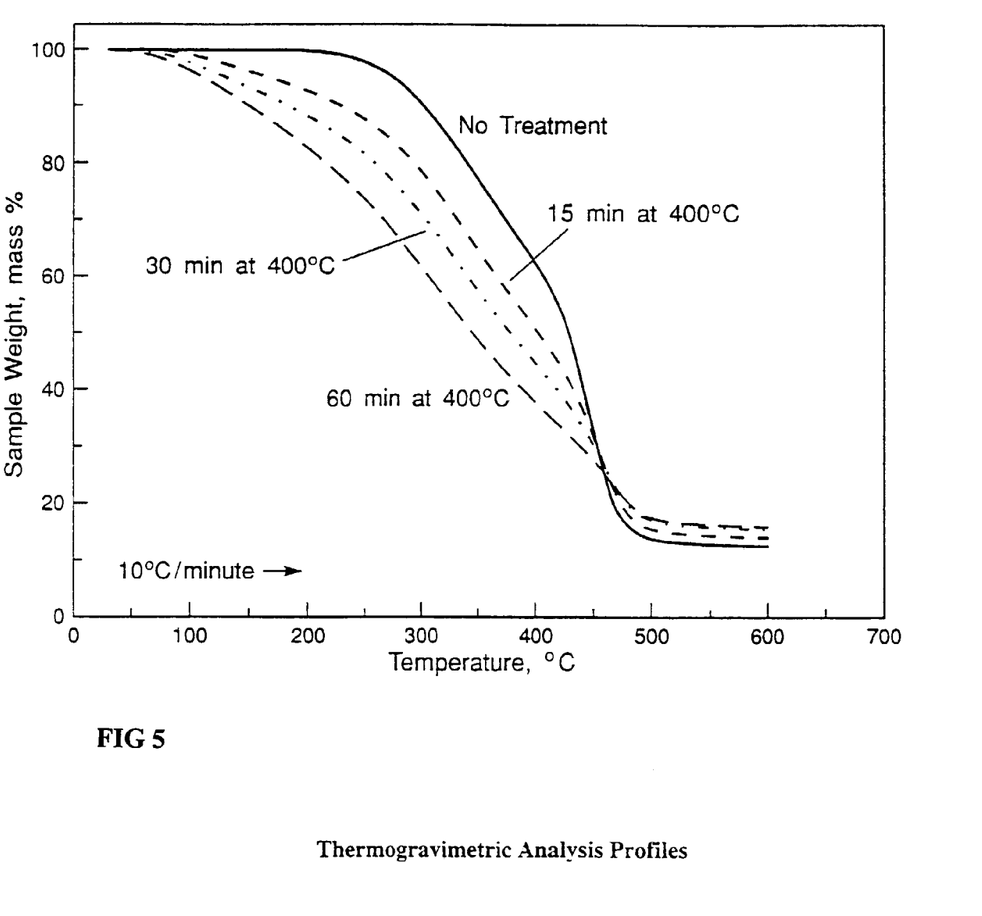
FIG. 5 provides a graph of thermogravimetric analysis profiles.

Now referring primarily to FIG. 5, thermogravimetric analysis profiles show increased losses of light components with increasing pyrolysis severity. This is not surprising since cracking reactions have taken place and lighter, distillable components have been formed. The weight loss and residue data are presented in Table 3. The weight losses at 400° C. provide an estimate of conversion of the residuum to lighter distillable products by pyrolysis. The residue is the carbonaceous material remaining in the pan at 600° C. This is analogous but not identical to coke formation as determined by the Conradson Carbon value for the original residuum (500° C.), which is 16.4 wt. %.

TABLE 3

Thermogravimetric Analysis Data

| Pyrolysis Time, min | Weight % Loss at 400° C. | Residue at 600° C., wt. % |
|---|---|---|
| 0 | 37.4 | 12.2 |
| 15 | 49.2 | 13.8 |
| 30 | 55.2 | 15.3 |
| 60 | 62.2 | 15.6 |

Figure 6:
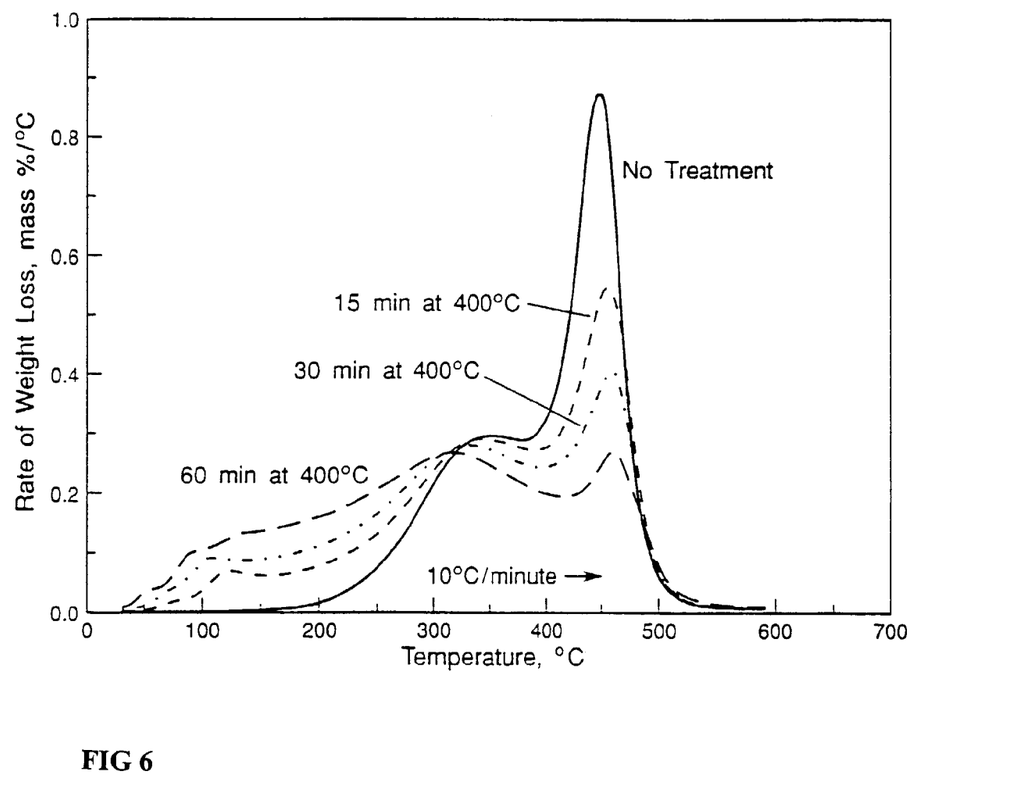
FIG. 6 provides a graph of differential plot of thermogravimetric analysis.

Now referring primarily to FIG. 6, derivative TGA profiles are shown. The profiles for the various oils are quite different and the results suggest that the progress of pyrolysis can be monitored by TGA analyses. There is a region near 310° C. where weight loss is about the same for the original and pyrolyzed materials. At temperatures above this, the rate of weight loss is higher for the unpyrolyzed material than the pyrolyzed material, and it decreases as pyrolysis time increases. This is due to the presence of more high boiling material in the original material than in the pyrolyzed materials. This high boiling material is cracked during pyrolysis to form lower boiling material. Below 310° C. the opposite effect is observed, with larger rates of weight loss of lower boiling material in the more severely pyrolyzed materials than in the less severely pyrolyzed materials and the original material.

A third method of assessing immediacy of petroleum residua to coke formation can be by ultrasonic spectroscopy (US). Ultrasonic spectroscopy can be used to evaluate various types of materials in a wide variety of configurations. For example, US can be used to evaluate the presence of water in oil; evaluate liquid levels; detect the presence of interface boundaries of two immiscible liquids; detect density or viscosity differences in liquids; determine particle sizes and amounts; assess the integrity of various solid materials relative to corrosion, cracking, or compositional changes; measure product consistency, such consistency of cheese, butter, and vegetable oil. See generally, McClements, D. J., "Ultrasonic Measurements in Particle Size Analysis", Encyclopedia of Analytical Chemistry, R. A. Meyers, ed., John Wiley & Sons, Chichester (1998), hereby incorporated by reference.

However, there are many applications of US that have not yet been explored and it was not known until the instant invention that US could be useful in making determinations with respect deposition phenomena during thermal treatment of petroleum residua. Importantly, the invention provides non-invasive, non-destructive US analysis apparatus and techniques which provide measurement parameters which correlate with the coking indexes set out above. Because there are no moving mechanical parts other than the oscillations associated with acoustical transducers the invention can be implemented in a modular form to monitor petroleum residua processing in situ, even implemented in situ to monitor refining of petroleum residua to generate lighter distillates.

The invention can comprise a plurality of ultrasonic waveforms having at least one ultrasonic waveform characteristic. Ultrasonic waveforms in accordance with embodiments of the invention can have wavelengths in the range of about 0.1 MHz to about 200 MHz. A narrow bandwidth frequency spectrum within the range can be generated or a wider bandwidth can be swept. The waveforms within the bandwidth frequency can be transmitted continuously or discontinuously as pulses or bursts, or can be intensity modulated. Ultrasonic waveforms having wavelengths in 0.1 MHz to 200 MHz range can be generated in accordance with the invention by various types of waveform generators including those selected from the non-limiting group of piezoelectric transducers, electromagnetic acoustic transducers, intensity modulated lazers, or the like. Regardless of the manner of generating wavelengths within the particular bandwidth frequency selected, the ultrasonic waveforms generated are coupled to the petroleum residuum or petroleum residua to be analyzed.

Interaction of the plurality of ultrasonic waveforms with the petroleum residua affect ultrasonic waveform characteristics. Certain embodiments of the invention measure the change in ultrasonic waveform velocity through the petroleum residua. The specific acoustic impedance is a function of the then existing petroleum residua density, and is expressed as:

$$Z = \rho V$$

where $\rho$ is the density and V is the waveform velocity.

Other embodiments of the invention can be based upon the alteration in the amplitude of the waveform, or attenuation of the waveform. Ultrasonic attenuation can be given in terms of Neper per distance x such as Neper/cm. This is calculated as $u = -1/x \, X \ln A_x/A_o$ where A is the signal amplitude at distance 0 and distance x. To obtain attenuation in decibels, Neper can be multiplied by 8.686. When ultrasonic waves are coupled to petroleum residua, ultrasonic waveform absorption (u) increases as asphaltenes become depleted of the associated resins. Even prior to asphaltene complex aggregation or solid deposition phenomena, ultrasonic waveform absorption in petroleum residua comprises the sum of two effects:

$$u = u_f + u_s$$

where $u_f$ is absorption due to internal friction between asphaltenes complexes within the petroleum residuum, and $u_s$ due to scattering by asphaltenes complexes. The average size of the asphaltene complex, D, and the frequency, v, have a significant effect on the scattering at a particular wavelength $\lambda$. For asphaltene complexes and agglomerated particles leading to coke formation in a petroleum residuum matrix, the average size is in the range of about 0.5–5 microns, depending on pyrolysis residence time. Schabron, J. et al. "Characterization of Residua During Pyrolysis", American Chemical Society, Petroleum Chemistry Division Preprints, 47(1), 17 (2002), hereby incorporated by reference herein.

For asphaltene complexes in petroleum residua when $\lambda$ is greater than D, $u_s$ is proportional to $D^3 v^4$; when $\lambda$ is about the same as D, $u_s$ is proportional to $Dv^2$; and when $\lambda$ is less than or equal to D, $u_s$ is proportional to $1/D$. In ultrasonic analysis of petroleum residua, the frequency range between about 0.1 MHz to about 200 MHz generates wavelengths in the range of about 1 nanometer (nm) to about 10 nm. Therefore, implementation of the invention as described provides the advantage of the first case in which the attenuation due to scattering is a function of the diameter of the asphaltene complex cubed.

Altered or attenuated waveform characteristics when generated in accordance with the invention can be coupled to an ultrasonic waveform detector which can be a discrete receiving transducer, or can be the ultrasonic waveform generator or transmitting transducer when waveforms are generated as pulses or bursts. The resulting signal can be digitized, subsampled, and reconstructed using fast Fourier Transformation to obtain altered amplitude or phase information which can be displayed or stored. Examples of continuous, burst, and pulse ultrasonic spectroscopy are generally disclosed for example by U.S. Pat. Nos. 5,305,239; 5,663,502; 4,305,294; 5,062,269; 5,591,913; 6,023,975; 6,057,927; 5,408,881; 4,790,188; 4,899,589; 5,251,486; 5,467,655; 4,659,224; and 4,966,459, each hereby incorporated herein.

With respect to the analysis of petroleum residua as described above suitable ultrasonic attenuation measurements can be obtained within a range of about 1 Mhz to about 3 MHz during pyrolytic thermal treatment using a variety of different ultrasonic spectroscopy instruments such as the HR-US 102 US spectrometer manufactured by Ultrasonic Scientific, Guiness Enterprise Centre, Taylor's Lane, Dublin 8, Ireland; or the Matec TB100 using a computer card as pulser and receiver as manufactured by Matec Instruments56 Hudson Street, Northborough, Mass. 01532 USA. Although the numerical values generated by each instrument cannot be directly compared with one another trends can be compared and each affords analysis of waveforms attenuated by asphaltene complexes in petroleum residua of sufficient quality to determine immediacy of a petroleum residua to formation of solid materials.

Three non-limiting examples of ultrasonic attenuation data between about 1 MHz to about 3 MHz was obtained of various petroleum residua thermally treated at 400° C. for 0 minutes, and between 15 minutes and 20 minutes utilizing the above mentioned instruments. Data were converted to Neper/cm ultrasonic attenuation and are set out in Table 2.

The results show that Neper/cm can be correlated to the above-described $P_a/C_{min}$ Coking and X/Y coking indexes.

TABLE 2

Ultrasonic Attenuation (1–3 mHz) for Original Petroleum Residua and Petroleum Residua Pyrolyzed at 400° C. (752 EF)

| Residuum | Pyrolysis Time, min. | WRI Coking Indexes Y/X | $p_a/C_{min}$ | US Attenuation Compared To Original Residuum, neper/cm |
|---|---|---|---|---|
| Boscan | 0 | 2.0 | 1.62 | 0.00 |
| (2–3 mHz) | 20 | 1.1 | 0.48 | −0.55 |
| Redwater, B.C. | 0 | 5.6 | 1.20 | 0.00 |
| (1 mHz) | 15 | 2.3 | 0.62 | −0.31 |
| Lloydminster | 0 | 3.0 | 1.12 | 0.00 |
| (1.3 mHz) | 20 | 1.3 | 0.36 | −1.85 |
|  | 20 | 1.1 | 0.15 | −2.11 |

Figure 7:
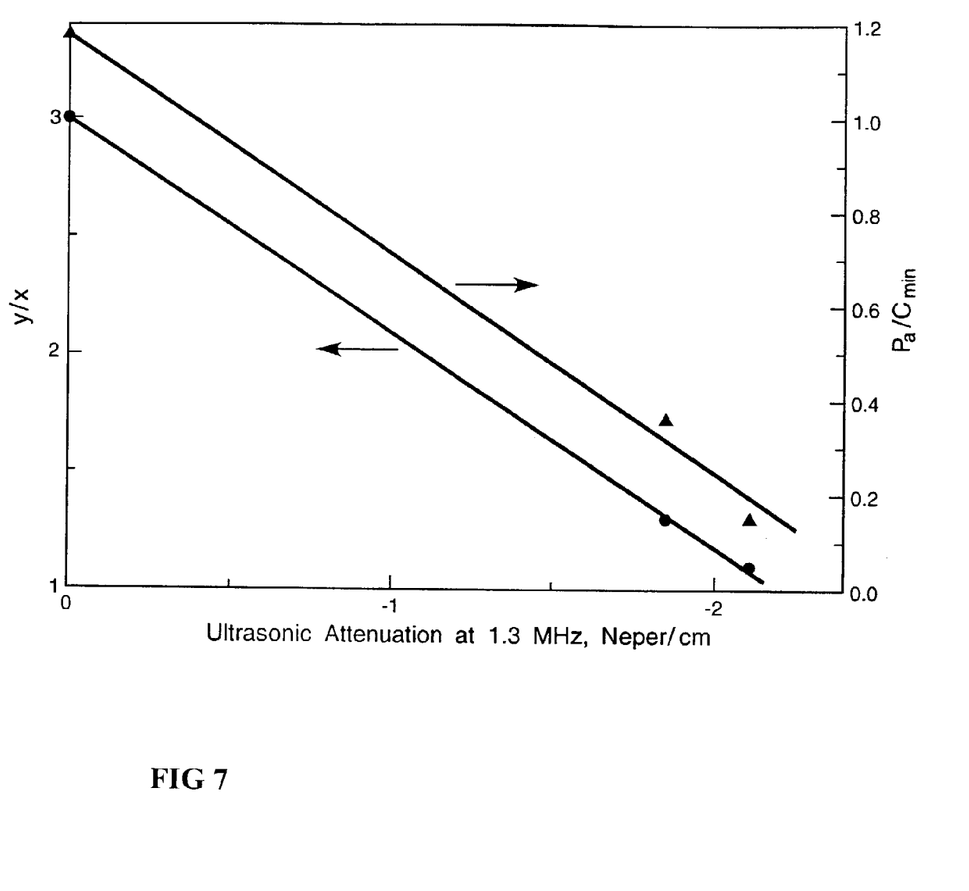
FIG. 7 provides a graph of coking indexes versus ultrasonic attenuation.

Now referring primarily to FIG. 7, ultrasonic attenuation spectra of petroleum residua during pyrolytic thermal treatment obtained in accordance with the invention and converted to Neper/cm shows the immediacy of the petroleum residua to deposition phenomena when correlated with the Y/X or $p_d/C_{min}$ coking indexes.

Understandably, now that this correlation has been shown a standard ultrasonic waveform attenuation curve for a given US instrument and US parameters in accordance with the invention can be prepared in advance of pyrolytic thermal treatment of petroleum residua. The invention can be implemented on-line (along with a sampler as described above) and employed continuously during pyrolytic thermal treatment of petroleum residua to provide sufficient data with respect to asphaltene complex properties to allow thermal treatment to proceed in the desired manner uninterrupted until the desired ultrasonic spectra are obtained. The predetermined end point for thermal treatment based upon US spectra may be selected to avoid deposition phenomena. However, the useful implementation of the invention need not be limited to determination of immediacy of a petroleum residua to deposition of solid materials, but can also be used to establish or maintain consistent petroleum residua properties when different types or kinds of petroleum residua are blended.

As can be easily understood from the foregoing, the basic concepts of the present invention may be embodied in a variety of ways. It involves calorimetry, thermogravimetric, and ultrasonic techniques as well as devices to accomplish the techniques which provide measures that relate to the then existing properties of asphaltene complexes in petroleum residua which can be used to maintain consistency of such properties during blending of petroleum residua or can be used to determine the immediacy of a petroleum residua to deposition phenomena such as coke formation.

In this application, the calorimetry, thermogravimetric, and ultrasonic techniques are disclosed as part of the results shown to be achieved by the various devices described and as steps that are inherent in their utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion is intended to serve as a basic description with sufficient numbers of examples to allow those skilled in the art to make and use the invention. The description may not explicitly describe all embodiments possible; many alternatives are implicit. The description along with the non-limiting examples also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in a subsequent non-provisional patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for the subsequent patent application.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of "an ultrasonic waveform generator" should be understood to encompass disclosure of the act of "generating a plurality of ultrasonic waveforms"—whether explicitly discussed or not—and, conversely, were there effectively disclosure of the act of "generating a plurality of ultrasonic waveforms", such a disclosure should be understood to encompass disclosure of a "an ultrasonic waveform generator" and even a "means for generating a plurality of ultrasonic waveforms" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, the content of all references set forth below or the content of the exhibits filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the calorimetry, thermogravimetric, and ultrasonic devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed.

We claim:

1. A method of assessing immediacy of a petroleum residuum to formation of coke particles in refinery processing comprising the steps of:
  a. providing an ultrasonic waveform generator;
  b. thermally treating said petroleum residuum;
  c. interacting at least one ultrasonic waveform from said ultrasonic waveform generator with said petroleum residuum;

d. detecting at least one ultrasonic waveform characteristic of said at least one ultrasonic waveform after passing through said petroleum residuum;

e. comparing said at least one ultrasonic waveform characteristic with a predetermined ultrasonic waveform characteristic that correlates to an onset of coke particle formation, wherein said predetermined ultrasonic waveform characteristic is determined for a test sample based on analysis selected from a group consisting of: at least one coke index, precipitation of coke, filtration, gravimetric, asphaltene flocculation titration, $p_a/C_{min}$, ratio of a weight percent of a cyclohexane soluble portion of heptane asphaltenes to a weight percent of heptane asphaltenes, solubility characteristics of asphaltenes, values of a weight percent of a cyclohexane soluble portion of heptane asphaltenes, pyrolysis time, relative viscosity, $K_S$ values, $K_F$ values, K values, and observing the test sample; and f. assessing immediacy of said petroleum residuum to formation of coke particles.

2. The method of claim 1 wherein said step (b) comprises thermally treating said petroleum residuum to create a pyrolysis system wherein said petroleum residuum is heated greater than about 650 degrees F. (about 340 degrees C.).

3. The method of claim 1 wherein said step (b) comprises thermally treating said petroleum residuum to generate lighter distillates.

4. The method of claim 1 wherein said step (b) comprises heating said petroleum residuum within the range of between about 480 degrees F. (about 250 degrees C.) and about 650 degrees F. (about 340 degrees C.).

5. The method of claim 1 wherein said step (c) comprises monitoring said petroleum residuum until said at least one ultrasonic waveform characteristic reaches said predetermined ultrasonic waveform characteristic.

6. The method of claim 1 wherein said step (c) comprises delivering pulses of said at least one ultrasonic waveform from said ultrasonic waveform generator to said petroleum residuum.

7. The method of claim 1 or 2 wherein said petroleum residuum is selected from a group consisting of resins, heavy oils, shale oils, coal tars, tar sand bitumen, asphalts, fuel oil that remains after the removal of lighter distillates, oils obtained from shale and oils obtained from tar sand bitumen.

8. The method of claim 1 wherein said step (a) comprises selecting said ultrasonic waveform generator from a group consisting of piezoelectric transducers, electromagnetic acoustic transducers, lasers and intensity modulated lasers.

9. The method of claim 1 wherein said step (c) comprises interacting said at least one ultrasonic waveform having a frequency in the range of about 0.1 MHz to about 200 MHz with said petroleum residuum.

10. The method of claim 1 wherein said step (c) comprises interacting said at least one ultrasonic waveform having a frequency in the range of about 1 MHz to about 3 MHz with said petroleum residuum.

11. The method of claim 1 wherein said step (d) comprises detecting said at least one ultrasonic waveform characteristic of said at least one ultrasonic waveform with an ultrasonic transducer.

12. The method of claim 1 wherein said step (d) comprises the step of applying fast Fourier Transformation to said at least one ultrasonic waveform characteristic.

13. The method of claim 1 or 12 wherein said at least one ultrasonic waveform characteristic is selected from a group consisting of velocity, attenuation, frequency, amplitude, and phase information.

14. The method of claim 1 wherein said step (f) comprises continuously assessing immediacy of said petroleum residuum to formation of coke particles.

15. The method of claim 14 further comprising assessing said at least one ultrasonic waveform characteristic of said petroleum residuum a sufficient number of times in a duration of time to avoid formation of said coke particles during said thermal treatment.

16. The method of claim 1 further comprising stopping said step (b) if said at least one ultrasonic waveform characteristic from said detected ultrasonic waveform equals said predetermined ultrasonic waveform characteristic.

17. The method of claim 14 further comprising continuing said step (b) if said at least one ultrasonic waveform characteristic from said detected ultrasonic waveform does not reach said predetermined ultrasonic waveform characteristic.

18. The method of claim 1 wherein said onset of coke particle formation comprises an existence of coke particles having a size selected from a group consisting of about 10 microns, greater than about 10 microns, about 0.5 microns, about 5 microns, and between about 0.5 microns and about 5 microns.

19. The method of claim 14 wherein said predetermined ultrasonic waveform characteristic is determined by a standard ultrasonic waveform attenuation curve.

20. The method of claim 1 wherein said standard ultrasonic waveform attenuation curve is specific to an ultrasonic instrument and ultrasonic parameters.

* * * * *

UNITED STATES PATENT AND TRADEMARK OFFICE
CERTIFICATE OF CORRECTION

| | |
|---|---|
| PATENT NO. | : 7,223,603 B2 |
| APPLICATION NO. | : 10/374779 |
| DATED | : May 29, 2007 |
| INVENTOR(S) | : Joseph F. Rovani, Jr. and John F. Schabron |

It is certified that error appears in the above-identified patent and that said Letters Patent is hereby corrected as shown below:

Title Page, Item (75)

"Thomas F. Turner, Laramie, WY (US)" should be deleted

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,223,603 B2 | Page 1 of 1 |
| APPLICATION NO. | : 10/374779 | |
| DATED | : May 29, 2007 | |
| INVENTOR(S) | : Joseph F. Rovani, Jr. et al. | |

It is certified that error appears in the above-identified patent and that said Letters Patent is hereby corrected as shown below:

*The following paragraph should appear at Column 1, line 8:*

ACKNOWLEDGMENT OF GOVERNMENT SUPPORT

This patent relates to work performed under U.S. DOE Cooperative Agreement #DE-FC26-98FT40322. The U.S. government may have certain rights in this inventive technology, including "march-in" rights, as provided for by the terms of U.S. DOE Cooperative Agreement #DE-FC26-98FT40322.

Signed and Sealed this

Thirteenth Day of July, 2010

David J. Kappos
*Director of the United States Patent and Trademark Office*